United States Patent [19]

Krenzer

[11] 4,023,957
[45] May 17, 1977

[54] HERBICIDAL 1-THIADIAZOLYL-5-CARBAMOYLOX-YIMIDAZOLIDINONES

[75] Inventor: John Krenzer, Oak Park, Ill.

[73] Assignee: Velsicol Chemical Corporation, Chicago, Ill.

[22] Filed: Sept. 10, 1975

[21] Appl. No.: 611,947

Related U.S. Application Data

[60] Division of Ser. No. 442,934, Feb. 15, 1974, Pat. No. 3,925,402, which is a continuation-in-part of Ser. No. 428,272, Dec. 26, 1973, abandoned.

[52] U.S. Cl. ................................................. 71/90
[51] Int. Cl.² ........................................ A01N 9/142
[58] Field of Search ........................................ 71/90

[56] References Cited

UNITED STATES PATENTS

| 3,759,939 | 9/1973 | Metzger et al. | 71/90 |
| 3,773,780 | 11/1973 | Metzger et al. | 71/90 |
| 3,849,432 | 11/1974 | Metzger et al. | 71/90 |

Primary Examiner—Lewis Gotts
Assistant Examiner—Catherine L. Mills
Attorney, Agent, or Firm—Robert J. Schwarz; Dietmar H. Olesch

[57] ABSTRACT

This invention discloses new compounds of the formula

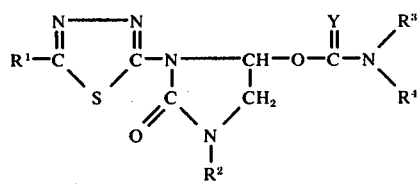

wherein $R^1$ is selected from the group consisting of alkyl, alkenyl, haloalkyl, alkoxy, alkylthio, alkylsulfonyl and alkylsulfinyl; $R^2$ is alkyl; $R^3$ is selected from the group consisting of hydrogen and alkyl; Y is selected from the group consisting of oxygen and sulfur; and $R^4$ is selected from the group consisting of hydrogen, alkyl, cycloalkyl and

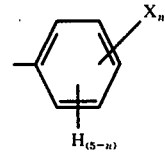

wherein X is selected from the group consisting of alkyl, halogen, haloalkyl and alkoxy, and n is an integer from 0 to 5.

2 Claims, No Drawings

HERBICIDAL 1-THIADIAZOLYL-5-CARBAMOYLOX-YIMIDAZOLIDINONES

This is a division of copending application Ser. No 442,934, filed Feb. 15, 1974 now U.S. Pat. No. 3,925,402, which is a continuation in part of Ser. No. 428,272, filed Dec. 26, 1973, now abandoned.

This invention relates to new compositions of matter and more particularly relates to new chemical compounds of the formula

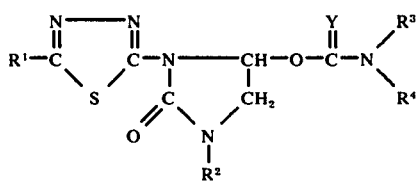 (I)

wherein $R^1$ is selected from the group consisting of alkyl, alkenyl, haloalkyl, alkoxy, alkylthio, alkylsulfonyl and alkylsulfinyl; $R^2$ is alkyl; $R^3$ is selected from the group consisting of hydrogen and alkyl; Y is selected from the group consisting of oxygen and sulfur; and $R^4$ is selected from the group consisting of hydrogen, alkyl, cycloalkyl and

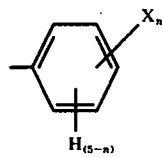

wherein X is selected from the group consisting of alkyl, halogen, haloalkyl and alkoxy, and n is an integer from 0 to 5.

The compounds of this invention are unexpectedly useful as herbicides.

In a preferred embodiment of the present invention $R^1$ is selected from the group consisting of lower alkyl, lower alkenyl, lower haloalkyl, lower alkoxy, lower alkylthio, lower alkylsulfonyl and lower alkylsulfinyl; $R^2$ is lower alkyl; $R^3$ is selected from the group consisting of hydrogen and lower alkyl; and $R^4$ is selected from the group consisting of hydrogen, lower alkyl, cycloalkyl of from 3 to 7 carbon atoms, and

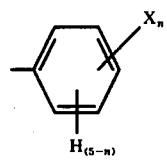

wherein X is selected from the group consisting of lower alkyl, halogen, lower haloalkyl and lower alkoxy, and n is an integer from 0 to 3.

The term lower as used herein designates a straight or branched carbon chain of up to six carbon atoms.

The compounds of the present invention wherein one of $R^3$ or $R^4$ is hydrogen can be prepared by reacting a compound of the formula

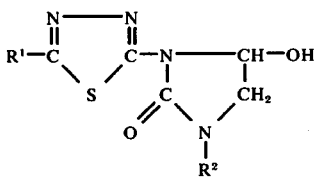 (II)

wherein $R^1$ and $R^2$ are as heretofore described, with an isocyanate or isothiocyanate of the formula

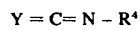 (III)

wherein Y and $R^4$ are as heretofore described with the exclusion of hydrogen. This reaction can be effected by combining the compound of formula II with about an equimolar or slight excess molar amount of the isocyanate of formula III at room temperature and in the presence of a catalytic amount of triethylamine. An inert organic solvent can be used if desirable. The reaction mixture can be stirred at room temperature or at elevated temperatures if the reaction proceeds slowly and then let stand for a period of up to about one hour to ensure completion of the reaction. After this time excess isocyanate if used can be removed by vacuum stripping to yield the desired product which can be used as such or can be further purified by conventional means such as washing, recrystallizing and the like.

The compounds of the present invention wherein neither $R^3$ nor $R^4$ is hydrogen can be prepared by reacting a compound of formula II as heretofore described with a carbamoyl chloride of the formula

 (IV)

wherein Y, $R^3$ and $R^4$ are as heretofore described except that neither $R^3$ nor $R^4$ is hydrogen. This reaction can be effected by combining about equimolar amounts of the compounds of formulae II and IV in an inert organic solvent such as toluene or xylene in the presence of an acid acceptor such as a tertiary amine. The reaction mixture can then be heated at reflux for a period of from about ½ to about 4 hours. After this the reaction mixture can be filtered to remove acid acceptor salt and can then be stripped of solvent under vacuum to yield the desired product as the residue. This product can be used as such or can be further purified by washing, recrystallizing and the like.

The compounds of the present invention wherein both $R^3$ and $R^4$ are hydrogen can be prepared by reacting a compound of formula II with potassium cyanate or potassium thiocyanate in the presence of concentrated acetic acid. This reaction can be effected by dispersing the compound of formula II in a reaction medium containing 90 percent acetic acid and 10 percent water. Powdered potassium cyanate can then be incrementally added with stirring at room temperature. After the addition is completed stirring can be continued for a period of from ½ to 2 hours to ensure completion of the reaction. Water can then be added to precipitate the product. After this time the desired product can be recovered as a precipitate by filtration and can be purified by washing with water and recrystallization.

The compounds of formula II can be readily prepared by heating a compound of the formula

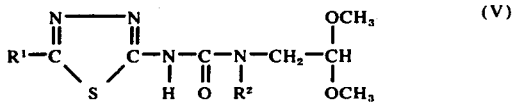 (V)

wherein R¹ and R² are as heretofore described, in a dilute, aqueous, acidic reaction medium for a period of about 10 to about 60 minutes. Temperatures of from 70° C to the reflux temperature of the reaction mixture can be utilized. The reaction medium can comprise a dilute aqueous inorganic acid such as hydrochloric acid at a concentration of from about 0.5 to about 5 percent. Upon completion of the reaction the desired product can be recovered as a precipitate by cooling the reaction mixture. This product can be used as such or can be further purified by conventional means such as recrystallization and the like.

The compounds of formula V can be prepared by reacting a molar amount of an isocyanate dimer of the formula

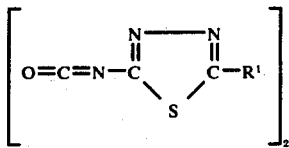 (VI)

wherein R¹ is as heretofore described, with about two molar amounts of a dimethyl acetal of the formula

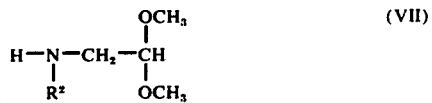 (VII)

wherein R² is as heretofore described. This reaction can be effected by heating a mixture of the isocyanate dimer and the acetal in an inert organic reaction medium such as benzene at the reflux temperature of the reaction mixture. Heating at reflux can be continued for a period of from about 2 to about 30 minutes to ensure completion of the reaction. After this time the desired product can be recovered upon evaporation of the reaction medium and can be used as such or can be further purified by standard techniques in the art.

The isocyanate dimer of formula VI can be prepared by reacting a thiadiazole of the formula

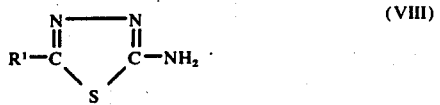 (VIII)

wherein R¹ is as heretofore described, with phosgene. This reaction can be effected by adding a slurry or solution of the thiadiazole, in a suitable organic solvent such as ethyl acetate, to a saturated solution of phosgene in an organic solvent such as ethyl acetate. The resulting mixture can be stirred at ambient temperatures for a period of from about 4 to about 24 hours. The reaction mixture can then be purged with nitrogen gas to remove unreacted phosgene. The desired product can then be recovered by filtration, if formed as a precipitate, or upon evaporation of the organic solvent used if soluble therein. This product can be used as such or can be further purified as desired.

Exemplary thiadiazoles of formula VIII useful for preparing the compounds of the present invention are: 5-methyl-2-amino-1,3,4-thiadiazole, 5-ethyl-2-amino-1,3,4-thiadiazole, 5-propyl-2-amino-1,3,4-thiadiazole, 5-t-butyl2-amino-1,3,4-thiadiazole, 5-allyl-2-amino-1,3,4-thiadiazole, 5-pent-3-enyl-2-amino-1,3,4-thiadiazole, 5-chloromethyl-2-amino-1,3,4-thiadiazole, 5-β-chloroethyl-2-amino-1,3,4-thiadiazole, 5-α-chloropropyl-2-amino-1,3,4-thiadiazole, 5-trichloromethyl-2-amino-1,3,4-thiadiazole, 5-trifluoromethyl-2-amino-1,3,4-thiadiazole, 5-methoxy-2-amino-1,3,4-thiadiazole, 5-ethoxy-2-amino-1,3,4-thiadiazole, 5-propoxy-2-amino-1,3,4-thiadiazole, 5-butyloxy-2-amino-1,3,4-thiadiazole, 5-hexyloxy-2-amino-1,3,4-thiadiazole, 5-methylthio-2-amino-1,3,4-thiadiazole, 5-ethylthio-2-amino-1,3,4-thiadiazole, 5-propylthio-2-amino-1,3,4-thiadiazole, 5-butylthio-2-amino-1,3,4-thiadiazole, 5-methylsulfonyl-2-amino-1,3,4-thiadiazole, 5-ethylsulfonyl-2-amino-1,3,4-thiadiazole, 5-butylsulfonyl-2-amino-1,3,4-thiadiazole, 5-methylsulfinyl-2-amino-1,3,4-thiadiazole, 5-ethylsulfinyl-2-amino-1,3,4-thiadiazole, 5-propylsulfinyl-2-amino-1,3,4-thiadiazole, 5butylsulfinyl-2-amino-1,3,4-thiadiazole, and the like.

Exemplary suitable acetals of formula VII for preparing the compounds of this invention are the dimethyl acetal of 2-methylaminoacetaldehyde, the dimethyl acetal of 2-ethylaminoacetaldehyde, the dimethyl acetal of 2-propylaminoacetaldehyde, the dimethyl acetal of 2butylaminoacetaldehyde, the dimethyl acetal of 2-pentylaminoacetaldehyde and the dimethyl acetal of 2-hexylaminoacetaldehyde.

Exemplary suitable isocyanates and isothiocyanates of formula III are methyl isocyanate, ethyl isocyanate, propyl isocyanate, butyl isocyanate, hexyl isocyanate, cyclopropyl isocyanate, cyclobutyl isocyanate, cyclopentyl isocyanate, cyclohexyl isocyanate, cycloheptyl isocyanate, phenyl isocyanate, 2-methylphenyl isocyanate, 4-ethylphenyl isocyanate, 4-butylphenyl isocyanate, 2-chlorophenyl isocyanate, 2,4-dichlorophenyl isocyanate, 4-bromophenyl isocyanate, 4-fluorophenyl isocyanate, 4-chloromethylphenyl isocyanate, 4-trifluoromethylphenyl isocyanate, 2-methoxyphenyl isocyanate, 2-ethoxyphenyl isocyanate, 2-propoxyphenyl isocyanate, 2-methyl-4-chlorophenyl isocyanate, 2-methoxy-3,6-dichlorophenyl isocyanate, methyl isothiocyanate, ethyl isothiocyanate, propyl isothiocyanate, butyl isothiocyanate, hexyl isothiocyanate, cyclopropyl isothiocyanate, cyclobutyl isothiocyanate, cyclopentyl isothiocyante, cyclohexyl isothiocyanate, cycloheptyl isothiocyanate, phenyl isothiocyanate, 2-methylphenyl isothiocyanate, 4-ethylphenyl isothiocyanate, 4-butylphenyl isothiocyanate, 2-chlorophenyl isothiocyanate, 2,4-dichlorophenyl isothiocyanate, 4-bromophenyl isothiocyanate, 4-fluorophenyl isothiocyanate, 4-chloromethylphenyl isothiocyanate, 4-trifluoromethylphenyl isothiocyanate, 2-methoxyphenyl isothiocyanate, 2-ethoxyphenyl isothiocyanate, 2-propoxyphenyl isothiocyanate, 2-methyl-4-chlorophenyl isothiocyanate, 2-methoxy-3,6-dichlorophenyl isothiocyanate and the like.

Exemplary suitable carbamoyl and thiocarbamoyl chlorides of formula IV are N,N-dimethylcarbamoyl chloride, N,N-diethylcarbamoylchloride, N,N-dipropylcarbamoyl chloride, N,N-dibutylcarbamoyl chloride, N,N-dihexylcarbamoyl chloride, N-methyl-N-cyclopropylcarbamoyl chloride, N-methyl-N-cyclohexylcarbamoyl chloride, N-methyl-N-cycloheptylcarbamoyl chloride, N-ethyl-N-cycloheptylcarbamoyl chloride, N-methyl-N-phenylcarbamoyl chloride, N-ethyl-N-phenylcarbamoyl chloride, N-methyl-N-(2-methylphenyl)carbamoyl chloride, N-methyl-N-(2-ethylphenyl)carbamoyl chloride, N-methyl-N-(2-propylphenyl)-carbamoyl chloride, N-methyl-N-(4-chlorophenyl)carbamoyl chloride, N-methyl-N-(4-bromophenyl)carbamoyl chloride, N-methyl-N-(2-methoxyphenyl)carbamoyl chloride, N-methyl-N-(4-trifluoromethylphenyl)carbamoyl chloride, N,N-dimethylthiocarbamoyl chloride, N,N-diethylthiocarbamoyl chloride, N,N-dipropylthiocarbamoyl chloride, N,N-dibutylthiocarbamoyl chloride, N,N-dihexylthiocarbamoyl chloride, N-methyl-N-cyclohexylthiocarbamoyl chloride, N-methyl-N-cycloheptylthiocarbamoyl chloride, N-ethyl-N-cycloheptylthiocarbamoyl chloride, N-methyl-N-phenylthiocarbamoyl chloride, N-ethyl-N-phenylthiocarbamoyl chloride, N-methyl-N-(2-methylphenyl)thiocarbamoyl chloride, N-methyl-N-(2-ethylphenyl)thiocarbamoyl chloride, N-methyl-N-(2-propylphenyl)thiocarbamoyl chloride, N-methyl-N-(4-chlorophenyl)thiocarbamoyl chloride, N-methyl-N-(4-bromophenyl)thicarbamoyl chloride, N-methyl-N-(2-methoxyphenyl)thiocarbamoyl chloride and N-methyl-N-(4-trifluoromethylphenyl)thiocarbamoyl chloride.

The manner in which the compounds of the present invention can be prepared is more specifically illustrated in the following examples.

EXAMPLE 1

Preparation of 5-Methyl-1,3,4-thiadiazol-2-yl Isocyanate Dimer

A saturated solution of phosgene in ethyl acetate (100 ml) is charged into a glass reaction vessel equipped with a mechanical stirrer. A slurry of 5-methyl-2-amino-1,3,4-thiadiazole (40 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-methyl-1,3,4-thiadiazol-2-yl isocyanate dimer.

EXAMPLE 2

Preparation of the Dimethyl Acetal of 2-[1-Methyl-3-(5-methyl-1,3,4-thiadiazol-2-yl)ureido]acetaldehyde A mixture of 5-methyl-1,3,4-thiadiazol-2-yl isocyanate dimer (0.05 mole), the dimethyl acetal of 2-methylaminoacetaldehyde (0.1 mole) and benzene (60 ml) are charged into a glass reaction vessel equipped with a mechanical stirrer and reflux condenser. The reaction mixer is heated at reflux for a period of about 15 minutes. After this time the mixture is stripped of benzene under reduced pressure to yield a solid product as the residue. The residue is then recrystallized to yield the desired product the dimethyl acetal of 2-[1-methyl-3-(5-methyl-1,3,4-thiadiazol-2-yl)ureido] acetaldehyde.

EXAMPLE 3

Preparation of 1-(5-Methyl-1,3,4-thiadiazol-2-yl)-3-methyl-5-hydroxy-1,3-imidazolidin-2-one The dimethyl acetal of 2-[1-methyl-3-(5-methyl-1,3,4-thiadiazol-2-yl)ureido] acetaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot and the filtrate is cooled to form a precipitate. The precipitate is recovered by filtration, is dried and is recrystallized to yield the desired product 1-(5-methyl-1,3,4-thiadiazol-2-yl)-3-methyl-5-hydroxy-1,3-imidazolidin-2-one.

EXAMPLE 4

Preparation of 1-(5-Methyl-1,3,4-thiadiazol-2-yl)-3-methyl-5-(N-methylcarbamoyloxy)-1,3-imidazolidin-2-one.

1-(5-Methyl-1,3,4-thiadiazol-2-yl)-3-methyl-5-hydroxy-1,3-imidazolidin-2-one (0.05 mole) and methyl isocyanate (3.5 ml; 0.06 mole) are charged into a glass reaction vessel equipped with a mechanical stirrer. The mixture is stirred and triethylamine (1 drop) is added. The reaction mixture is then allowed to stand for a period of about 1 hour. After this time the product is washed with hexane to yield the desired product 1-(5-methyl-1,3,4-thiadiazol-2-yl)-3-methyl-5-(N-methylcarbamoyloxy)-1,3-imidazolidin-2-one.

EXAMPLE 5

Preparation of 5-t-Butyl-1,3,4-thiadiazol-2-yl Isocyanate Dimer

A saturated solution of phosgene in ethyl acetate (100 ml) was charged into a glass reaction vessel equipped with a mechanical stirrer. A slurry of 5-t-butyl-2-amino-1,3,4-thiadiazole (10 grams) in ethyl acetate (300 ml) was added to the reaction vessel and the resulting mixture was stirred for a period of about 16 hours resulting in the formation of a precipitate. The reaction mixture was then purged with nitrogen gas to remove unreacted phosgene. The purged mixture was then filtered to recover the desired product 5-t-butyl-1,3,4-thiadiazol-2-yl-isocyanate dimer as a solid having a melting point of 261 to 263° C.

EXAMPLE 6

Preparation of the Dimethyl Acetal of 2-[1-Methyl-3-(5-t-butyl-1,3,4-thiadiazol-2-yl)ureido]acetaldehyde A mixture of 5-t-butyl-1,3,4-thiadiazol-2-yl isocyanate dimer (6 grams), the dimethyl acetal of 2-methylaminoacetaldehyde (3.9 grams) and benzene (50 ml) was charged into a glass reaction flask equipped with a mechanical stirrer and reflux condenser. The reaction mixture was heated at reflux, with stirring for a period of about 5 minutes. After this time the reaction mixture was stripped of benzene to yield an oil which solidified upon standing. The resulting solid was then recrystallized from pentane to yield the desired product the dimethyl acetal of 2-[1methyl-3-(5-t-butyl-1,3,4-thiadiazol-2-yl)ureido]acetaldehyde having a melting point of 80°–82° C.

EXAMPLE 7

Preparation of
1-(5-t-Butyl-1,3,4-thiadiazol-2-yl)-3-methyl-5-hydroxy-1,3-imidazolidin-2-one The dimethyl acetal of 2-[1-methyl-3-(5-t-butyl-1,3,4-thiadiazol-2-yl)ureido]acetaldehyde (16 grams), concentrated hydrochloric acid (10 ml) and water (500 ml) were charged into a glass reaction vessel equipped with a mechanical stirrer, thermometer and reflux condenser. The reaction mixture was heated at reflux for a period of about 15 minutes. The reaction mixture was filtered while hot and the filtrate was then cooled, resulting in the formation of a precipitate. The precipitate was recovered by filtration, dried and was recrystallized from a benzene-hexane mixture to yield the desired product (1-(5-t-butyl-1,3,4-thiadiazol-2-yl)-3-methyl-5-hydroxy-1,3-imidazolidin-2-one having melting point of 133° to 134° C.

EXAMPLE 8

Preparation of
1(5-t-Butyl-1,3,4-thiadiazol-2-yl)-3-methyl-5-(N-methylcarbamoyloxy)-1,3-imidazolidin-2-one 1-(5-t-Butyl-1,3,4-thiadiazol-2-yl)-3-methyl-5-hydroxy-1,3-imidazolidin-2-one (4 grams) and methyl isocyanate (5 ml) were charged into a glass reaction vessel equipped with a mechanical stirrer. The mixture was stirred until homogeneous and triethylamine (1 drop) was added thereto. The reaction mixture was then allowed to stand for 1 hour. The reaction mixture was then stripped of excess isocyanate and the remaining solid was recrystallized from isopropyl alcohol to yield the desired product 1-(5-t-butyl-1,3,4-thiadiazol-2-yl)-3-methyl-5-(N-methylcarbamoyloxy)-1,3-imidazolidin-2-one having a melting point of 195° to 198° C.

EXAMPLE 9

Preparation of 5-Trifluoromethyl-1,3,4-thiadiazol-2-yl Iosocyanate Dimer

A saturated solution of phosgene in ethyl acetate (100 ml) was charged into a glass reaction vessel equipped with a mechanical stirrer. A slurry of 5-trifluoromethyl-2-amino-1,3,4-thiadiazole (45 grams) in ethyl acetate (300 ml) was added to the reaction vessel and the resulting mixture was stirred for a period of about 16 hours resulting in the formation of precipitate. The reaction mixture was then purged with nitrogen gas to remove unreacted phosgene. The purged mixture was filtered to recover 48 grams of a white solid. This solid was recrystallized from dimethyl formamide to yield the desired product 5-trifluoromethyl-1,3,4-thiadiazol-2-yl isocyanate dimer.

EXAMPLE 10

Preparation of the Dimethyl Acetal of
2-[1-Methyl-3-(5-trifluoromethyl-1,3,4-thiadiazol-2-yl)ureido]acetaldehyde A mixture of 5-trifluoromethyl-1,3,4-thiadiazol-2-yl isocyanate dimer (9.5 grams), the dimethyl acetal of 2-methylaminoacetaldehyde (5.8 grams) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. This product was recrystallized from heptane to yield the desired product the dimethyl acetal of 2-[1-methyl-3-(5-trifluoromethyl-1,3,4-thiadiazol-2-yl)ureido]acetaldehyde having a melting point of 101° to 102° C.

EXAMPLE 11

Preparation of
1-(5-Trifluoromethyl-1,3,4-thiadiazol-2-yl)-3-methyl-5-hydroxy-1,3-imidazolidin-2-one The dimethyl acetal of 2-[1-methyl-3-(5-trifluoromethyl-1,3,4-thiadiazol-2-yl)ureido]acetaldehyde (15 grams), water (400 ml) and hydrochloric acid (4 ml) were charged into a glass reaction vessel equipped with a mechanical stirrer, thermometer and reflux condenser. The reaction mixture was heated at reflux for a period of about 15 minutes. The reaction mixture was then filtered while hot and the filtrate was cooled resulting in the formation of a precipitate. The precipitate was recovered by filtration, was dried and was recrystallized from an ethyl acetate-hexane mixture to yield the desired product 1-(5-trifluoromethyl-1,3,4-thiadiazol-2-yl)-3-methyl-5-hydroxy-1,3-imidazolidin-2-one having a melting point of 136° to 138° C.

EXAMPLE 12

Preparation of 1-(5-Trifluoromethyl-1,3,4-thiadiazol-2-yl)-3-methyl-5-(N-methylcarbamoyloxy)-1,3-imidazolidin-2-one 1-(5-Trifluoromethyl-1,3,4-thiadiazol-2-yl)-3-methyl-5-hydroxy-1,3-imidazolidin-2-one (4grams) and methyl isocyanate (3 ml) were charged into a glass reaction vessel. The mixture was stirred until homogeneous and triethylamine (1 drop) was added. The mixture was then allowed to stand for a period of about 1 hour. After this time the resulting product was washed with hexane and recrystallized from an ethyl acetate-hexane mixture to yield the desired product 1-(5-trifluoromethyl-1,3,4-thiadiazol-2-yl)-3-methyl-5-(N-methylcarbamoyloxy)-1,3-imidazolidin-2-one having a melting point of 163° to 165° C.

EXAMPLE 13

Preparation of
1-(5-Trifluoromethyl-1,3,4-thiadiazol-2-yl)-3-methyl-5-(N-phenylcarbamoyloxy)-1,3-imidazolidin-2-one 1-(5-Trifluoromethyl-1,3,4-thiadiazol-2-yl)-3-methyl-5-hydroxy-1,3-imidazolidin-2-one (4 grams) and phenyl isocyanate were charged into a glass reaction vessel. The mixture was stirred until homogeneous and triethylamine (1 drop) was added. The mixture was then allowed to stant for one-half hour. After this time the resulting product was washed with hexane and was then recrystallized from an ethyl acetate-heptane mixture to yield the desired product 1-(5-trifluoromethyl-1,3,4-thiadiazol-2-yl)-3-methyl-5-(N-phenylcarbamoyloxy)-1,3-imidazolidin-2-one having a melting point of 180° to 182° C.

EXAMPLE 14

Preparation of 5-Methoxy-1,3,4-thiadiazol-2-yl Isocyanate Dimer

A saturated solution of phosgene in ethyl acetate (100 ml) is charged into a glass reaction vessel equipped with a mechanical stirrer. A slurry of 5- methoxy-2-amino-1,3,4-thiadiazole (40 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-methoxy-1,3,4-thiadiazol-2-yl isocyanate dimer.

EXAMPLE 15

Preparation of the Dimethyl Acetal of 2-[1-Ethyl-3-(5-methoxy-1,3,4-thiadiazol-2-yl)ureido]acetaldehyde A mixture of 5-methoxy-1,3,4-thiadiazol-2-yl isocyanate dimer (0.05 mole), the dimethyl acetal of 2-ethylaminoacetaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product the dimethyl acetal of 2-[1-ethyl-3-(5-methoxy-1,3,4-thiadiazol-2-yl)ureido]acetaldehyde.

EXAMPLE 16

Preparation of 1-(5-Methoxy-1,3,4-thiadiazol-2-yl)-3-ethyl-5-hydroxy-1,3-imidazolidin-2-one The dimethyl acetal of 2-[1-ethyl-3-(5-methoxy-1,3,4-thiadiazol-2-yl)ureido] acetaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot and the filtrate is cooled to form a precipitate. The precipitate is recovered by filtration, is dried and is recrystallized to yield the desired product 1-(5-methoxy-1,3,4-thiadiazol-2-yl)-3-ethyl-5-hydroxy-1,3-imidazolidin-2-one.

EXAMPLE 17

Preparation of 1-(5-Methoxy-1,3,4-thiadiazol-2-yl)-3-ethyl-5-[N-(3,4-dichlorophenyl)carbamoyloxy]-1,3-imidazolidin-2-one 1-(5-Methoxy-1,3,4-thiadiazol-2-yl)-3-ethyl-5-hydroxy-1,3-imidazolidin-2-one (0.05 mole) and 3,4-dichlorophenyl isocyanate (0.06 mole) are charged into a glass reaction vessel. The mixture is stirred until homogeneous and triethylamine (1 drop) is added. The mixture is then allowed to stand for about 1 hour. After this time the resulting product is washed with hexane and is recrystallized to yield the desired product 1-(5-methoxy-1,3,4-thiadiazol-2-yl)-3-ethyl-5-[N-(3,4-dichlorophenyl)carbamoyloxy]-1,3-imidazolidin-2-one.

EXAMPLE 18

Preparation of 5-Methylthio-1,3,4-thiadiazol-2-yl Isocyanate Dimer

A saturated solution of phosgene in ethyl acetate (100 ml) is charged into a glass reaction vessel equipped with a mechanical stirrer. A slurry of 5-methylthio-2-amino-1,3,4-thiadiazole (45 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is filtered to recover the precipitate. The precipitate is then recrystallized to yield the desired product 5-methylthio-1,3,4-thiadiazol-2-yl isocyanate dimer.

EXAMPLE 19

Preparation of the Dimethyl Acetal of 2-[1-Propyl-3-(5-methylthio-1,3,4-thiadiazol-2-yl)ureido] acetaldehyde A mixture of 5-methylthio-1,3,4-thiadiazol-2-yl isocyanate dimer (0.05 mole), the dimethyl acetal of 2-propylaminoacetaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product the dimethyl acetal of 2-[1-propyl-3-(5-methylthio-1,3,4-thiadiazol-2-yl)ureido] acetaldehyde.

EXAMPLE 20

Preparation of 1-(5-Methylthio-1,3,4-thiadiazol-2-yl)-3-propyl-5-hydroxy-1,3-imidazolidin-2-one The dimethyl acetal of 2-[1-propyl-3-(5-methylthio-1,3,4-thiadiazol-2-yl)ureido] acetaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot and the filtrate is cooled to form a precipitate. The precipitate is recovered by filtration, is dried and is recrystallized to yield the desired product 1-(5-methylthio-1,3,4-thiadiazol-2-yl)-3-propyl-5-hydroxy-1,3-imidazolidin-2-one.

EXAMPLE 21

Preparation of 1-(5-Methylthio-1,3,4-thiadiazol-2-yl)-3-propyl-5-(N,N-dimethylcarbamoyloxy)-1,3-imidazolidin-2-one 1-(5-Methylthio-1,3,4-thiadiazol-2-yl)-3-propyl-5-hydroxy-1,3-imidazolidin-2-one (0.05 mole), N,N-dimethylcarbamoyl chloride (0.06 mole), pyridine (0.06 mole) and xylene (150 ml) are charged into a glass reaction vessel equipped with a mechanical stirrer, thermometer and reflux condenser. The reaction mixture is heated at reflux with stirring for a period of about 2 hours. After this time the mixture is cooled to room temperature and filtered to remove pyridine hydrochloride. The filtrate is then stripped of solvent under reduced pressure and the resulting residue is recrystallized to yield the desired product 1-(5-methylthio-1,3,4-thiadiazol-2-yl)-3-propyl-5-(N,N-dimethylcarbamoyloxy)-1,3-imidazolidin-2-one.

EXAMPLE 22

Preparation of 5-Methylsulfonyl-1,3,4-thiadiazol-2-yl Isocyanate Dimer

A saturated solution of phosgene in ethyl acetate (100 ml) is charged into a glass reaction vessel equipped with a mechanical stirrer. A slurry of 5-methylsulfonyl-2-amino-1,3,4-thiadiazole (50 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-methylsulfonyl-1,3,4-thiadiazol-2-yl isocyanate dimer.

EXAMPLE 23

Preparation of the Dimethyl Acetal of 2-[1-Methyl-3-(5-methylsulfonyl-1,3,4-thiadiazol-2-yl)ureido] acetaldehyde A mixture of 5-methylsulfonyl-1,3,4-thiadiazol-2-yl isocyanate dimer (0.05 mole), the dimethyl acetal of 2-methylaminoacetaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product the dimethyl acetal of 2-[1-methyl-3-(5-methylsulfonyl-1,3,4-thiadiazol-2-yl)ureido] acetaldehyde.

EXAMPLE 24

Preparation of 1-(5-Methylsulfonyl-1,3,4-thiadiazol-2-yl)-3-methyl-5-hydroxy-1,3-imidazolidin-2-one The dimethyl acetal of 2-[1-methyl-3-(5-methylsulfonyl-1,3,4-thiadiazol-2-yl)ureido] acetaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot and the filtrate is cooled to form a precipitate. The precipitate is recovered by filtration, is dried and is recrystallized to yield the desired product 1-(5-methylsulfonyl-1,3,4-thiadiazol-2-yl)-3-methyl-5-hydroxy-1,3-imidazolidin-2-one.

EXAMPLE 25

Preparation of 1-(5-Methylsulfonyl-1,3,4-thiadiazol-2-yl)-3-methyl-5-[N-methyl-N-(3-chlorophenyl) carbamoyloxy]-1,3-imidazolidin-2-one 1-(5-Methysulfonyl-1,3,4-thiadiazol-2-yl)-3-methyl-5-hydroxy-1,3-imidazolidin-2-one (0.05 mole), N-methyl-N-(4-chlorophenyl)carbamoyl chloride (0.06 mole), pyridine (0.06 mole) and toluene (125 ml) are charged into a glass reaction vessel equipped with a mechanical stirrer, thermometer and reflux condenser. The reaction mixture is heated at reflux with stirring for a period of about 3 hours. After this time the reaction mixture is cooled to room temperature and is filtered to remove pyridine hydrochloride. The filtrate is then washed with water, dried over anhydrous magnesium sulfate and and stripped of solvent leaving a residue. The residue is recrystallized to yield the desired product 1-(5-methylsulfonyl-1,3,4-thiadiazol-2-yl)-3-methyl-5-[N-methyl-N-(3-chlorophenyl)-carbamoyloxy]-1,3-imidazolidin-2-one.

EXAMPLE 26

Preparation of 5-Methylsulfinyl-1,3,4-thiadiazol-2-yl Isocyanate Dimer

A saturated solution of phosgene in ethyl acetate (100 ml) is charged into a glass reaction vessel equipped with a mechanical stirrer. A slurry of 5-methylsulfinyl-2-amino-1,3,4-thiadiazole (50 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-methylsulfinyl-1,3,4-thiadiazol-2-yl isocyanate dimer.

EXAMPLE 27

Preparation of the Dimethyl Acetal of 2-[1-Methyl-3-(5-methyl-sulfinyl-1,3,4-thiadiazol-2-yl)ureido] acetaldehyde A mixture of 5-methylsulfinyl-1,3,4-thiadiazol-2-yl isocyanate dimer (0.05 mole), the dimethyl acetal of 2-methylaminoacetaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product the dimethyl acetal of 2-[1-methyl-3-(5-methylsulfinyl-1,3,4-thiadiazol-2-yl)ureido]-acetaldehyde.

EXAMPLE 28

Preparation of 1-(5-Methylsulfinyl-1,3,4-thiadiazol-2-yl)-3-methyl-5-hydroxy-1,3-imidazolidin-2-one The dimethyl acetal of 2-[1-methyl-3-(5-methylsulfinyl-1,3,4-thiadiazol-2-yl)ureido] acetaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot and the filtrate is cooled to form a precipitate. The precipitate is recovered by filtration, is dried and is recrystallized to yield the desired product 1-(5-methylsulfinyl-1,3,4-thiadiazol-2-yl)-3-methyl-5-hydroxy-1,3-imidazolidin-2-one.

EXAMPLE 29

Preparation of 1-(5-Methylsulfinyl-1,3,4-thiadiazol-2-yl)-3-methyl-5-(N-methyl-N-cyclohexylcarbamoyloxy)-1,3-imidazolidin-2-one 1-(5-Methylsulfinyl-1,3,4-thiadiazol-2-yl)-3-methyl-5-hydroxy-1,3-imidazolidin-2-one (0.05 mole), N-methyl-N-cyclohexylcarbamoyl chloride (0.06 mole), pyridine (0.06 mole) and toluene (150 ml) are charged into a glass reaction vessel equipped with a mechanical stirrer, thermometer and reflux condenser. The reaction mixture is heated at reflux with stirring for a period of about 3 hours. After this time the reaction mixture is cooled to room temperature and is filtered to remove pyridine hydrochloride. The filtrate is then washed with water, dried over anhydrous magnesium sulfate and stripped of solvent leaving a residue. The residue is recrystallized to yield the desired product 1-(5-methylsulfinyl-1,3,4-thiadiazol-2-yl)-3-methyl-5-N-methyl-N-cyclohexylcarbamoyloxy)-1,3-imidazolidin-2-one.

EXAMPLE 30

Preparation of
1-(5-t-Butyl-1,3,4-thiadiazol-2-yl)-3-methyl-5-carbamoyloxy-1,3-imidazolidin-2-one 1-(5-t-Butyl-1,3,4-thiadiazol-2-yl)-3-methyl-5-hydroxy-1,3-imidazolidin-2-one (0.05 mole) dispersed in concentrated aqueous acetic acid (90% concentration; 125 ml) is charged into a glass reaction vessel equipped with a mechanical stirrer. The reaction mixture is stirred at room temperature and powdered potassium cyanate (0.06 mole) is incrementally added over a period of ten minutes. After the addition is completed stirring is continued for a period of about 1 hour to ensure completion of the reaction. After this time the reaction mixture is filtered to recover the product that has formed. This product is then washed with dilute aqueous potassium carbonate and with water and is then recrystallized to yield the desired product 1-(5-t-butyl-1,3,4-thiadiazol-2-yl)-3-methyl-5-carbamoyloxy-1,3-imidazolidin-2-one.

EXAMPLE 31

Preparation of
1-(5-Methyl-1,3,4-thiadiazol-2-yl)-3-methyl-5-(N-methylthiocarbamoyloxy)-1,3-imidazolidin-2-one 1-(5-Methyl-1,3,4-thiadiazol-2-yl)-3-methyl-5-hydroxy-1,3-imidazolidin-2-one (0.05 mole) and methyl isothiocyanate (3.5 ml; 0.06 mole) are charged into a glass reaction vessel equipped with a mechanical stirrer. The mixture is stirred and triethylamine (1 drop) is added. The reaction mixture is then allowed to stand for a period of about 1 hour. After this time the product is washed with hexane to yield the desired product 1-(5-methyl-1,3,4-thiadiazol-2-yl)-3-methyl-5-(N-methylthiocarbamoyloxy)-1,3-imidazolidin-2-one.

EXAMPLE 32

Preparation of
1-(5-t-Butyl-1,3,4-thiadiazol-2-yl)-3-methyl-5-(N-methylthiocarbamoyloxy)-1,3-imidazolidin-2-one 1-(5-t-Butyl-1,3,4-thiadiazol-2-yl)-3-methyl-5-hydroxy-1,3-imidazolidin-2-one (4 grams) and methyl isothiocyanate (5 ml) are charged into a glass reaction vessel equipped with a mechanical stirrer. The mixture is stirred until homogeneous and triethylamine (1 drop) is added thereto. The reaction mixture is then stripped of excess isothiocyanate and the remaining solid is recrystallized to yield the desired product 1-(5-t-butyl-1,3,4-thiadiazol-2-yl)-3-methyl-5-(N-methylthiocarbamoyloxy)-1,3-imidazolidin-2-one.

EXAMPLE 33

Preparation of
1-(5-Trifluoromethyl-1,3,4-thiadiazol-2-yl)-3-methyl-5-(N-phenylthiocarbamoyloxy)-1,3-imidazolidin-2-one 1-(5-Trifluoromethyl-1,3,4-thiadiazol-2-yl)-3-methyl-5-hydroxy-1,3-imidazolidin-2-one (4 grams) and phenyl isothiocyanate are charged into a glass reaction vessel. The mixture is stirred until homogeneous and triethylamine (1 drop) is added. The mixture is then allowed to stand for ½ hour. After this time the resulting product is washed with hexane and is then recrystallized to yield the desired product 1-(5-trifluoromethyl-1,3,4-thiadiazol-2-yl)-3-methyl-5-(N-phenylthiocarbamoyloxy)-1,3-imidazolidin-2-one.

EXAMPLE 34

Preparation of
1-(5-Methoxy-1,3,4-thiadiazol-2-yl)-3-ethyl-5-[N-(3,4-dichlorophenyl)thiocarbamoyloxy]-1,3-imidazolidin-2-one 1-(5-Methoxy-1,3,4-thiadiazol-2-yl)-3-ethyl-5-hydroxy-1,3-imidazolidin-2-one (0.05 mole) and 3,4-dichlorophenyl isothiocyanate (0.06 mole) are charged into a glass reaction vessel. The mixture is stirred until homogeneous and triethylamine (1 drop) is added. The mixture is then allowed to stand for about 1 hour. After this time the resulting product is washed with hexane and is recrystallized to yield the desired product 1-(5-methoxy-1,3,4-thiadiazol-2-yl)-3-ethyl-5-[N-(3,4-dichlorophenyl)thiocarbamoyloxy]-1,3-imidazolidin-2-one.

EXAMPLE 35

Preparation of
1-(5-Methylthio-1,3,4-thiadiazol-2-yl)-3-propyl-5-(N,N-dimethylthiocarbamoyloxy)-1,3-imidazolidin-2-one 1-(5-Methylthio-1,3,4-thiadiazol-2-yl)-3-propyl-5-hydroxy-1,3-imidazolidin-2-one (0.05 mole), N,N-dimethylthiocarbamoyl chloride (0.06 mole), pyridine (0.06 mole) and xylene (150 ml) are charged into a glass reaction vessel equipped with a mechanical stirrer, thermometer and reflux condenser. The reaction mixture is heated at reflux with stirring for a period of about 2 hours. After this time the mixture is cooled to room temperature and filtered to remove pyridine hydrochloride. The filtrate is then stripped of solvent under reduced pressure and the resulting residue is recrystallized to yield the desired product 1-(5-methylthio-1,3,4-thiadiazol-2-yl)-3-propyl-5-(N,N-dimethylthiocarbamoyloxy)-1,3- imidazolidin-2-one.

Additional compounds within the scope of the present invention which can be prepared by the procedures detailed in the foregoing examples are 1-(5-ethyl-1,3,4-thiadiazol-2-yl)-3-methyl-5-(N-ethylcarbamoyloxy)-1,3-imidazolidin-2-one, 1-(5-isopropyl-1,3,4-thiadiazol-2-yl)-3-butyl-5-(N-propylcarbamoyloxy)-1,3-imidazolidin-2-one, 1-(5-hexyl-1,3,4-thiadiazol-2-yl)-3-hexyl-5-(N-hexylcarbamoyloxy)-1,3-imidazolidin-2-one, 1-(5-allyl-1,3,4-thiadiazol-2-yl)-3-methyl-5-N-cyclopropylcarbamoyloxy)-1,3-imidazolidin-2-one, 1-(5-pent-3-enyl-1,3,4-thiadiazol-2-yl)-3-methyl-5-(N-cyclobutylcarbamoyloxyl)-1,3-imidazolidin-2-one, 1-(5-hex-4-enyl-1,3,4-thiadiazol-2-yl)-3-methyl-5-(N-cyclopentylcarbamoyloxy)-1,3- imidazolidin-2-one, 1-(5-β-chloroethyl-1,3,4-thiadiazol-2-yl)-3-methyl-5-(N-cycloheptylcarbamoyloxy)-1,3-imidazolidin-2-one, 1-(5γ-bromopropyl-1,3,4-thiadiazol-2-yl)-3-methyl-5-N,N-diethylcarbamoyloxy)-1,3imidazolidin-2-one, 1-(5-ethoxy-1,3,4-thiadiazol-2-yl)-3-methyl-5-[N-(2-methylphenyl)carbamoyloxy]-1,3-imidazolidin-2-one, 1-(5-propoxy-1,3,4-thiadiazol-2-yl)-3-methyl-5-[N-(2-ethylphenyl)-carbamoyloxy]-1,3-imidazolidin-2-one, 1-(5-hexyloxy-1,3,4-thiadiazol-2-yl)-3-methyl-5-[N-(4-butylphenyl)-carbamoyloxy]-1,3-imidazolidin-2-one, 1-(5-ethylthio-1,3,4-thiadiazol-2-yl)-3-methyl-5-[N-(4hexylphenyl)-carbamoyloxy]-1,3-imidazolidin-2-one, 1-(5-butylthio-1,3,4-thiadiazol-2-yl)-3-methyl-5-[N-(2,4-dimethylphenyl)carbamoyloxy]-1,3-imidazolidin-2-one, 1-(5-hexylthio-1,3,4-thiadiazol-2-yl)-3-methyl-5-[N-(4-bromophenyl)carbamoyloxy]-1,3-imidazolidin-2-one, 1-(5-methylsulfonyl-1,3,4-thiadiazol-2-yl)-3-methyl-5-[N-(4-iodophenyl)carbamoyloxy]-1,3-imidazolidin-2-one, 1-(5-ethylsulfonyl-1,3,4-thiadiazol-2-yl)-3-methyl-5-[N-(4-fluorophenyl)carbamoyloxy]-1,3-imidazolidin-2-one, 1-(5-propylsulfonyl-1,3,4-thiadiazol-2-yl)-3-methyl-5-[N-(4-trifluoromethyl-phenyl)carbamoyloxy]-1,3-imidazolidin-2-one, 1-(5-hexylsulfonyl-1,3,4-thiadiazol-2-yl)-3-methyl-5-[N-(4-trichloromethylphenyl)carbamoyloxy]-1,3-imidazolidin-2-one, 1-(5-ethylsulfinyl-1,3,4-thiadiazol-2-yl)-3-methyl-5-[N-(2-methoxyphenyl)carbamoyloxy]-1,3-imidazolidin-2-one, 1-(5-propylsulfinyl-1,3,4-thiadiazol-2-yl)-3-methyl-5-[N-(2-ethoxyphenyl)carbamoyloxy]-1,3-imidazolidin-2-one, 1-(5-butylsulfinyl-1,3,4-thiadiazol-2-yl)-3-methyl-5-[N-(3-propoxyphenyl)carbamoyloxy]-1,3-imidazolidin-2-one, 1-(5-hexylsulfinyl-1,3,4-thiadiazol-2-yl)-3-methyl-5-[N-(3-hexyloxyphenyl)carbamoyloxy]-1,3-imidazolidin-2-one, 1-(5-t-butylsulfinyl-1,3,4-thiadiazol-2-yl)-3-methyl-5-[N-(2,4,6-trichlorophenyl)carbamoyloxy]-1,3-imidazolidin-2-one, 1-(5-hexyl-1,3,4-thiadiazol-2-yl)-3-hexyl-5-(N-hexylthiocarbamoyloxy-1,3-imidazolidin-2-one, 1-(5-hex-4-enyl-1,3,4-thiadiazol-2-yl)-3-methyl-5-(N-cyclopentylthiocarbamoyloxy)-1,3-imidazolidin-2-one, 1-(5-ethoxy-1,3,4-thiadiazol-2-yl)-3-methyl-5-[N-(2-methylphenyl)thiocarbamoyloxy]-1,3-imidazolidin-2-one, 1-(5-ethylthio-1,3,4-thiadiazol-2-yl)-3-methyl-5[N-(4-hexylphenyl)thiocarbamoyloxy]-1,3-imidazolidin-2-one, 1-(5methylsulfonyl-1,3,4-thiadiazol-2-yl)-3-methyl-5-[N-(4-iodophenyl)thiocarbamoyloxy]-1,3-imidazolidin-2-one, 1-(5-hexylsulfonyl-1,3,4-thiadiazol-2-yl)-3-methyl-5-[N-(4-trichloromethylphenyl)-thiocarbamoyloxy]-1,3-imidazolidin-2-one 1-(5-butylsulfinyl-1,3,4-thiadiazol-2-yl)-3-methyl-5-[N-(3-propoxyphenyl)thiocarbamoyloxy]-1,3-imidazolidin-2-one.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under super-atmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal composition according to this invention is illustrated by the following example, in which the quantities are in parts by weight.

EXAMPLE 36

| Preparation of a Dust | |
|---|---|
| Product of Example 4 | 10 |
| Powdered Talc | 90 |

The above ingredients are mixed in a mechanical grinder-blender and are ground until a homogeneous, freeflowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, dessicants, growth inhibitors, and the like in the herbicidal compositions heretofore described. These other materials can comprise from about 5% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, 4-(2,4-DB), 2,4-DEB, 4-CPB, 4-CPA, 4-CPP, 2,4,5-TB, 2,4,5-TES, 3,4-DA, silvex and the like; carbamate herbicides such as IPC, CIPC, swep, barban, BCPC, CEPC, CPPC, and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazine herbicides such as simazine, chlorazine, atraone, desmetryne, norazine, ipazine, prometryn, atazine, trietazine, simetone, prometone, propazine, ametryne and the like; chloroacetamide herbicides such as alpha-chloro-N, N-dimethylacetamide, CDEA, CDAA, alpha-chloro-N-isopropylacetamide, 2-chloro-N-isopropylacetanilide, 4-(chloroacetyl)morpholine, 1-(chloroacetyl) piperidine, and the like; chlorinated aliphatic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, tricamba, amiben, fenac, PBA, 2-methoxy-3,6-dichlorophenylacetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamid, dipropalin, trifluralin, solan dicryl, merphos, DMPA, DSMA, MSMA, potassium azide, acrolein, benefin, bensulide, AMS, bromacil, 2(3,4-dichlorophenyl)-4-methyl-1,2,4-oxadiazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like.

Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters, foxtail, crabgrass, wild mustard, field pennycress, ryegrass, goose-grass, chickeed, wild oats, velvetleaf, purslane, barnyard grass, smmartweed, knotweed, cocklebur, wild buckwheat, kochia, medic, corn cockle, ragweed, sowthistle, coffeeweed, croton, cuphea, dodder, fumitory, groundsel, hemp nettle, knawel, spurge, spurry, emex, jungle rice, pondweed, dog fennel, carpetweed, morning glory, bedstraw, ducksalad, naiad, cheatgrass, fall panicum, jimsonweed, witchgrass, switchgrass, watergrass, teaweed, wild turnip and sprangletop; biennials such as wild carrot, matricaria, wild barley, campion, chamomile, burdock, mullein, roundleaved mallow, bull thistle, hounds-tongue, moth mullein and purple star thistle; or perennials such as white cockle, perennial ryegrass, quackgrass, Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail, winter-cress, horsenettle, nutsedge, milkweed and sicklepod.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively nontoxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of an active compound per acre may be required for good control of a dense infestation of hardy perennial weeds growing under favorable conditions.

The herbicidal toxicity of the new compounds of this invention can be illustrated by many of the established testing techniques known to the art, such as pre- and postemergence testing.

The herbicidal activity of the compounds of this invention was demonstrated by experiments carried out for the pre-emergence control of a variety of weeds. In these experiments small plastic greenhouse pots filled with dry soil were seeded with the various weed seeds. Twenty-four hours or less after seeding the pots were sprayed with water until the soil was wet and the test compounds formulated as aqueous emulsions of acetone solutions containing emulsifiers were sprayed at the indicated concentrations on the surface of the soil.

After spraying, the soil containers were placed in the greenhouse and provided with supplementary heat as required and daily or more frequent watering. The plants were maintained under these conditions for a period of from 15 to 21 days, at which time the condition of the plants and the degree of injury to the plants was rated on a scale of from 0 to 10, as follows: 0 = no injury, 1,2 = slight injury, 3,4 = moderate injury, 5,6 = moderately severe injury, 7,8,9 = severe injury and 10 = death. The effectiveness of these compounds is demonstrated by the following data:

TABLE I

| Test Compound | Concentration (lbs./acre) of Compound | INJURY RATING* | | | | | | | | | | | | |
|---|---|---|---|---|---|---|---|---|---|---|---|---|---|---|
| | | YNSG | WOAT | JMWD | VTLF | JNGS | PIGW | MSTD | YLFX | WRGS | CBGS | CTGS | MNGY | BNGS |
| Product of Example 8 | 10 | 9.5 | 9.5 | 9.0 | 9.0 | 9.5 | 10 | 10 | 9.5 | 9.5 | 10 | 10 | 10 | — |
| | 2 | 10 | 10 | 9.5 | 10 | 10 | 10 | 10 | 9.5 | — | 10 | 10 | 10 | 9.5 |
| | 1 | 10 | 10 | 9.5 | 10 | 9.5 | 10 | 10 | 9.5 | — | 10 | 10 | 10 | 9.5 |
| | 1/4 | 3.25 | 8.0 | 8.0 | 10 | 4.75 | 9.5 | 10 | 8.5 | — | 3.5 | 8.75 | 7.0 | 8.75 |
| | 1/8 | 0 | 3.5 | 5.5 | 5.0 | 0.5 | 8.0 | 9.0 | 1.0 | — | 0 | 7.0 | 1.0 | 1.0 |
| Product of Example 12 | 10 | 7.5 | 8.5 | 9.5 | 10 | 8.0 | 9.5 | 10 | 9.5 | 9.0 | 1.0 | 10 | 10 | — |
| | 4 | 2.5 | 5.0 | 9.5 | 10 | 4.5 | 10 | 10 | 9.5 | — | — | 9.0 | 7.5 | 4.0 |
| | 2 | 0 | 1.0 | 7.5 | 7.5 | 0 | 9.0 | 9.5 | 1.0 | — | — | 7.0 | 4.0 | 1.0 |
| | 1 | 0 | 1.0 | 5.0 | 5.0 | 0 | 6.0 | 8.5 | 0 | — | — | 3.5 | 2.0 | 0 |
| Product of Example 13 | 10 | 8.5 | 9.0 | 10 | 9.5 | 5.0 | 9.5 | 10 | 10 | 9.5 | 2.5 | 10 | 10 | — |
| | 4 | 0 | 9.5 | 10 | 10 | — | 10 | 10 | 9.5 | — | — | 9.5 | 6.0 | 1.0 |
| | 2 | 0 | 3.5 | 9.5 | 9.0 | — | 10 | 10 | 2.5 | — | — | 6.0 | 2.5 | 0 |
| | 1 | 0 | 3.0 | 9.5 | 9.5 | — | 10 | 10 | 3.5 | — | — | 6.0 | 0.5 | 0 |

*Values are averages of two or more replicates
YNSG: Yellow Nutsedge
WOAT: Wild Oats
JMWD: Jimsonweed
VTLF: Velvet Leaf
JNGS: Johnsongrass
PIGW: Pigweed
MSTD: Mustard
YLFX: Yellow Foxtail
WRGS: Watergrass
CBGS: Crabgrass
CTGS: Cheatgrass
MNGY: Morningglory
BNGS: Barnyardgrass The herbicidal activity of the compounds of this invention was also demonstrated by experiments carried out for the post-emergence control of a variety of weeds. In these experiments the compounds to be tested were formulated as aqueous emulsions and sprayed at the indicated dosage on the foliage of the weeds that have attained a prescribed size. After spraying the plants were placed in a greenhouse and watered daily or more frequently. Water was not applied to the foliage of the treated plants. The severity of the injury was determined 10 to 15 days after treatment and was rated on the scale of from 0 to 10 heretofore described. The effectiveness of these compounds is demonstrated by the following data:

TABLE II

| Test Compound | Concentration (lbs./acre) of Compound | INJURY RATING* | | | | | | | | |
|---|---|---|---|---|---|---|---|---|---|---|
| | | YNSG | WOAT | JMWD | VTLF | JNGS | PIGW | MSTD | YLFX | WRGS |
| Product of Example 8 | 10 | 10 | 10 | 10 | | 10 | 10 | 10 | 10 | 10 |
| | 2 | 10 | 10 | 10 | | 10 | 10 | 10 | 10 | — |
| | 1/2 | 10 | 10 | 10 | | 9.0 | 10 | 10 | 8.5 | — |
| | 1/16 | 0 | 9.0 | 6.0 | | 1.5 | 1.0 | 10 | 0 | — |
| Product of Example 12 | 10 | 0 | 3 | 10 | — | 2 | 5 | 10 | 0 | 2 |
| | 4 | — | — | 10 | 9 | — | — | 10 | — | — |
| Product of Example 13 | 10 | 0 | 8 | 10 | — | 0 | 4 | 9 | 0 | 0 |
| | 4 | — | — | 10 | 10 | — | — | 10 | — | — |

| | | CBGS | CTGS | MNGY | BDWD | BNGS | LMQR | COFW | CKBR | BKWT |
|---|---|---|---|---|---|---|---|---|---|---|
| Product of Example 8 | 10 | 10 | | 10 | 10 | — | | | | |
| | 2 | 9.5 | | 10 | 9.5 | 10 | | | | |
| | 1/2 | 1.0 | | 10 | 8.0 | 4.5 | | | | |
| | 1/16 | 0 | | 3.5 | 2.5 | 0 | | | | |
| Product of Example 12 | 10 | 0 | | 3 | 6 | | — | — | — | — |
| | 4 | — | | — | — | | 10 | 9 | 3 | 10 |
| Product of Example 13 | 10 | 0 | 2 | 0 | 3 | | — | — | — | — |
| | 4 | — | — | — | — | | 10 | 9 | 1 | 10 |

*Values may be averages of two replicates
YNGS: Yellow Nutsedge
MSTD: Mustard
BDWD: Binweed
WOAT: Wild Oats
YLFX: Yellow Foxtail
BNGS: Barnyardgrass
JMWD: Jimsonweed
WRGS: Watergrass
LMQR: Lambsquarter
VTLF: Velvet Leaf
CBGS: Crabgrass
COFW: Coffeeweed
JNGS: Johnsongrass
CTGS: Cheatgrass
CKBR: Cocklebur
PIGW: Pigweed
MNGY: Morningglory
BKWT: Buckwheat

I claim:
1. A herbicidal composition comprising an inert carrier, and as an essential active ingredient, in a quantity toxic to weeds, a compound of the formula

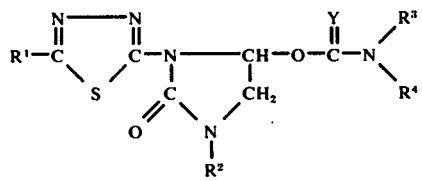

wherein $R_1$ is selected from the group consisting of lower alkyl, lower alkenyl, lower haloalkyl, lower alkoxy, lower alkylthio, lower alkylsulfonyl and lower alkylsulfinyl; $R^2$ is lower alkyl; $R^3$ is selected from the group consisting of hydrogen and lower alkyl; Y is selected from the group consisting of oxygen and sulfur; and $R^4$ is selected from the group consisting of hydrogen, lower alkyl, cycloalkyl of from 3 to 7 carbon atoms and

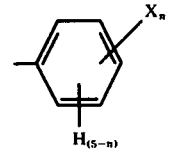

wherein X is selected from the group consisting of lower alkyl, halogen, lower haloalkyl and lower alkoxy, and $n$ is an integer from 0 to 3.

2. A method of controlling weeds which comprises contacting said weeds with a herbicidal composition of Claim 1.

* * * * *